United States Patent
Chen et al.

(10) Patent No.: US 11,162,131 B2
(45) Date of Patent: Nov. 2, 2021

(54) ASYMMETRIC TEMPLATES AND ASYMMETRIC METHOD OF NUCLEIC ACID SEQUENCING

(71) Applicant: Roche Sequencing Solutions, Inc., Pleasanton, CA (US)

(72) Inventors: Rui Chen, Fremont, CA (US); Toumy Guettouche, Pleasanton, CA (US); Loida Navarro, Dublin, CA (US); Aaron Richardson, Palo Alto, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 315 days.

(21) Appl. No.: 16/252,558

(22) Filed: Jan. 18, 2019

(65) Prior Publication Data
US 2019/0153515 A1    May 23, 2019

Related U.S. Application Data

(63) Continuation of application No. PCT/EP2017/068087, filed on Jul. 18, 2017.
(Continued)

(51) Int. Cl.
| | |
|---|---|
| *C12P 19/34* | (2006.01) |
| *C12Q 1/6806* | (2018.01) |
| *C12Q 1/6855* | (2018.01) |
| *C12N 15/10* | (2006.01) |
| *C12Q 1/683* | (2018.01) |
| *C12Q 1/6869* | (2018.01) |

(Continued)

(52) U.S. Cl.
CPC ....... *C12Q 1/6806* (2013.01); *C12N 15/1068* (2013.01); *C12Q 1/683* (2013.01); *C12Q 1/6855* (2013.01); *C12Q 1/6869* (2013.01); *C40B 40/06* (2013.01); *C40B 50/14* (2013.01); *C12Q 2525/155* (2013.01); *C12Q 2525/191* (2013.01); *C12Q 2525/301* (2013.01); *C12Q 2525/307* (2013.01); *C12Q 2535/122* (2013.01); *C12Q 2537/163* (2013.01); *C12Q 2565/519* (2013.01)

(58) Field of Classification Search
CPC ................ C12Q 1/6869; C12Q 1/6855; C12Q 2525/301
See application file for complete search history.

(56) References Cited

U.S. PATENT DOCUMENTS

| | | | |
|---|---|---|---|
| 7,302,146 | B2 | 11/2007 | Turner et al. |
| 8,153,375 | B2 | 4/2012 | Travers et al. |
| | | (Continued) | |

FOREIGN PATENT DOCUMENTS

| | | |
|---|---|---|
| WO | 2009/120372 A2 | 10/2009 |
| WO | 2011/055232 A2 | 5/2011 |
| WO | 2016/037389 A1 | 3/2016 |

OTHER PUBLICATIONS

International Search Report and Written Opinion dated Nov. 2, 2017 in corresponding PCT/EP2017/068087 filed Jul. 18, 2017, pp. 1-13.

*Primary Examiner* — Kenneth R Horlick
(74) *Attorney, Agent, or Firm* — Eric Grant Lee; Olga Kay

(57) ABSTRACT

The invention is a novel method of making and using a template for nucleic acid sequencing. The templates include circular and linear templates with symmetric and asymmetric adaptors. The methods include utilizing the templates in an asymmetric fashion.

15 Claims, 13 Drawing Sheets

Specification includes a Sequence Listing.

Related U.S. Application Data

(60) Provisional application No. 62/363,653, filed on Jul. 18, 2016.

(51) Int. Cl.
*C40B 40/06* (2006.01)
*C40B 50/14* (2006.01)

(56) References Cited

U.S. PATENT DOCUMENTS

| | | | |
|---|---|---|---|
| 2015/0031024 A1* | 1/2015 | Olsen | C12Q 1/6869 435/6.11 |
| 2017/0037465 A1* | 2/2017 | Tsavachidou | C12Q 1/6869 |

* cited by examiner

ASYMMETRIC TEMPLATES AND ASYMMETRIC METHOD OF NUCLEIC ACID SEQUENCING

RELATED APPLICATIONS

This application is a continuation of International Patent Application No. PCT/EP/2017/068087, filed Jul. 18, 2017, which is based on and claims the benefit of U.S. Provisional Application Ser. No. 62/363,653, filed on Jul. 18, 2016, the contents of which are hereby incorporated in their entirety.

SEQUENCE LISTING INCORPORATION BY REFERENCE

This application hereby incorporates-by-reference a sequence listing submitted herewith in a computer-readable format, having a file name of P33719US1_ST25, created on Jan. 18, 2019, which is 2,646 bytes in size.

FIELD OF THE INVENTION

The invention relates to the field of nucleic acid sequencing and more specifically, to preparing circular templates for nucleic acid sequencing.

BACKGROUND OF THE INVENTION

The use of circular templates for sequencing is known in the art. For example, Pacific Biosciences uses a SMRT-Bell™ adaptor to produce such templates. See U.S. Pat. Nos. 7,302,146 and 8,153,375. Circular single-stranded templates have several advantages in sequencing by synthesis: if a sequencing polymerase can perform rolling circle replication, the template will be read multiple times and both Watson and Crick strands will be read. The multiple reads of paired strands promises more accurate consensus sequence output. However, the existing circular templates are designed to bind two sequencing polymerases to each template. The two polymerases have the potential to interfere with each other and cause stalling or termination of synthesis generating suboptimal sequencing data. The present invention improves upon the existing technology to enable more accurate sequencing reads.

SUMMARY OF THE INVENTION

In some embodiments, the invention is a method of determining a sequence of a double-stranded target nucleic acid in a sample, comprising: contacting the sample comprising the double-stranded target nucleic acid with hairpin adaptor molecules comprising a double-stranded stem region and a single-stranded loop region; ligating each terminus of the target nucleic acid molecule to the double-stranded region of the adaptor molecule thereby forming a circular joint molecule comprising the target nucleic acid and having a double-stranded region and a proximal single-stranded loop region and a distal single-stranded loop region covalently linked to the double-stranded region; contacting the sample with a limiting concentration of blocking oligonucleotides tethered to solid support wherein the blocking oligonucleotide is non-extendable by a nucleic acid polymerase and is complementary to the proximal and a distal single-stranded loop regions, thereby capturing the circular joint molecule on the solid support and blocking the proximal single-stranded loop region; contacting the sample with oligonucleotide primer complementary to proximal and a distal single-stranded loop regions, thereby hybridizing the primer to the distal single-stranded loop region; extending the primer with a sequencing polymerase thereby determining the sequence of the double-stranded target nucleic acid. In some embodiments, the termini of the target nucleic acid and the adaptor are blunt. In some embodiments, the termini of the target nucleic acid and the adaptor are rendered cohesive by enzymatic treatment. The enzymatic treatment may be nucleotide addition and digesting the target nucleic acid and the adaptor with a restriction endonuclease. The blocking oligonucleotide may be tethered to the solid support via means selected from a covalent bond with the support molecule or a non-covalent bond with the support molecule. The non-covalent bond with the support molecule may be a specific interaction selected from biotin-streptavidin, antibody-antigen or hybridization of the blocking oligonucleotide to a complementary oligonucleotide covalently or non-covalently linked to the solid support. The blocking oligonucleotide may be non-extendable by the nucleic acid polymerase. The blocking oligonucleotide may be rendered non-extendable by the nucleic acid polymerase by a chemical modification selected from 3'-H, 2'-phosphate and 3'-phosphate. The blocking oligonucleotide may have a modification preventing binding of a nucleic acid polymerase. The blocking oligonucleotide may be non-extendable by a nucleic acid polymerase by virtue of being linked to the solid support via its 3'-end. The blocking oligonucleotide may comprise one or more duplex-stabilizing modifications such as LNA, PNA and non-natural nucleotides. The blocking oligonucleotide comprises one or more modifications blocking nuclease digestion such as a phosphorothioate backbone. Each particle of solid support is linked to multiple blocker oligonucleotides. In some embodiments, the method may further comprise a step of removing the circular molecules not captured on the solid support. The sequencing may be single molecule sequencing, sequencing by synthesis, nanopore sequencing or tunneling recognition sequencing. In some embodiments, extending the primer is by a strand displacing polymerase or by rolling circle replication. In some embodiments, the double-stranded target nucleic acid is generated in vitro from a single-stranded target nucleic acid.

In some embodiments, the invention is a method of determining a sequence of a double-stranded target nucleic acid in a sample, comprising: contacting the sample comprising the double-stranded target nucleic acid with a mixture of first and second hairpin adaptor molecules, each comprising a double-stranded stem region and a first single-stranded loop region or a second single-stranded loop region; ligating each terminus of the target nucleic acid molecule to the double-stranded region of the adaptor molecules thereby forming a circular joint molecule comprising the target nucleic acid and having a double-stranded region and the first single-stranded loop region on one end and the second single-stranded loop region on the other end covalently linked to the double-stranded region; contacting the sample with a limiting concentration of blocking oligonucleotides tethered to solid support wherein the blocking oligonucleotide is non-extendable by a nucleic acid polymerase and is complementary to the first single-stranded loop region, thereby capturing the circular molecule on the solid support and blocking the first single-stranded loop region; contacting the sample with an oligonucleotide primer complementary to the second single-stranded loop region, thereby hybridizing the primer to the second single-stranded loop region; extending the primer with a sequencing polymerase thereby determining the sequence of the double-stranded target nucleic acid. The termini of the target nucleic acid and the adaptor may be blunt, or rendered cohesive by enzymatic treatment that may be selected from nucleotide addition and digesting the target nucleic acid and the adaptor with a restriction endonuclease. In some embodiments, the blocking oligonucleotide is tethered to the solid support via means selected from a covalent bond with the support molecule or a non-covalent bond with the support molecule. The non-covalent bond with the support molecule may be a specific interaction selected from biotin-streptavidin, antibody-antigen or hybridization of the blocking oligonucleotide to a complementary oligonucleotide covalently or non-covalently linked to the solid support. The blocking oligonucleotide may be non-extendable by the nucleic acid polymerase due to e.g., a chemical modification selected from 3'-H, 2'-phosphate and 3'-phosphate. The blocking oligonucleotide may have a modification preventing binding of a nucleic acid polymerase. The blocking oligonucleotide may be non-extendable by a nucleic acid polymerase by virtue of being linked to the solid support via its 3'-end. The blocking oligonucleotide may comprise one or more duplex-stabilizing modifications such as e.g., linked nucleic acid (LNA), peptide nucleic acid (PNA) and a non-natural nucleotide. The blocking oligonucleotide may comprise one or more modifications blocking nuclease digestion e.g., a phosphorothioate backbone. In some embodiments, each particle of solid support is linked to multiple blocker oligonucleotides. In some embodiments, the method further comprises removing the nucleic acids not captured on the solid support. In some embodiments, sequencing is single molecule sequencing, sequencing by synthesis, nanopore sequencing or tunneling recognition sequencing. In some embodiments, extending the primer is by a strand displacing polymerase or by rolling circle replication. In some embodiments, the double-stranded target nucleic acid is generated in vitro from a single-stranded target nucleic acid.

In some embodiments, the invention is a method of determining a sequence of a double-stranded target nucleic acid in a sample, comprising: contacting the sample comprising the double-stranded target nucleic acid having two 5'-ends and two extendable 3'-ends with a terminal transferase, a single extendable nucleotide species, and providing means for controlling nucleotide incorporation by the terminal transferase, extending the extendable 3'-ends by incorporating multiple units of the single nucleotide thereby forming a linear joint molecule comprising the target nucleic acid and having a double-stranded region and a proximal and a distal single-stranded homopolymer regions; contacting the sample with a limiting concentration of capture oligonucleotide tethered to solid support wherein the capture oligonucleotide is complementary to the proximal and a distal single-stranded homopolymer regions thereby capturing the linear molecule on the solid support; contacting the sample with an oligonucleotide primer complementary to proximal and distal single-stranded homopolymer regions, thereby hybridizing the primer to the distal single-stranded homopolymer region; extending the primer with a sequencing polymerase thereby determining the sequence of the double-stranded target nucleic acid. The means for controlling nucleotide incorporation by the terminal transferase is the presence in the reaction a terminator nucleotide species at a ratio favoring the extendable nucleotide, or the time of the incorporation reaction. In some embodiments, the capture oligonucleotide is extendable and the method further comprises extending the capture oligonucleotide to reach the terminus of the target nucleic acid. The method may further comprise a step of ligating the extended capture oligonucleotide with the terminus of the target nucleic acid to create a continuous nucleic acid strand. The blocking oligonucleotide may be tethered to the solid support via means selected from a covalent bond with the support molecule or a non-covalent bond with the support molecule. The non-covalent bond with the support molecule may be a specific interaction selected from biotin-streptavidin, antibody-antigen or hybridization of the blocking oligonucleotide to a complementary oligonucleotide covalently or non-covalently linked to the solid support. In some embodiments, the blocking oligonucleotide comprises one or more duplex-stabilizing modifications such as linked nucleic acid (LNA), peptide nucleic acid (PNA) and a non-natural nucleotide. In some embodiments, the blocking oligonucleotide comprises one or more modifications blocking nuclease digestion, e.g., a phosphorothioate backbone. In some embodiments, each particle of solid support is linked to multiple blocker oligonucleotides. In some embodiments, the method further comprises a step of removing the nucleic acids not captured on the solid support. In some embodiments, each linear molecule has two different homopolymers created by blocking a proximal end of the target nucleic acid while extending the distal end with a mixture comprising the first non-terminator nucleotide, unblocking the proximal end and extending the proximal end with a mixture comprising the second non-terminator nucleotide. In some embodiments, the sequencing is single molecule sequencing, sequencing by synthesis, nanopore sequencing or tunneling recognition sequencing. In some embodiments, the double-stranded target nucleic acid is generated in vitro from a single-stranded target nucleic acid.

In some embodiments, the invention is a composition for determining a sequence of a double-stranded target nucleic acid comprising: a circular joint molecule comprising the target nucleic acid ligated at each end to an adaptor molecule comprising a double-stranded stem region and a single-stranded loop region, the circular joint molecule having a double-stranded region and a proximal single-stranded loop region and a distal single-stranded loop region covalently linked to the double-stranded region; a blocking oligonucleotide tethered to solid support wherein the blocking oligonucleotide is non-extendable by a nucleic acid polymerase and is hybridized to the proximal single-stranded loop region, thereby capturing the circular joint molecule on the solid support and blocking the proximal single-stranded loop region; an oligonucleotide primer hybridized to the distal single-stranded loop region; and a sequencing polymerase.

In some embodiments, the invention is a composition for determining a sequence of a double-stranded target nucleic acid comprising: a linear joint molecule comprising the target nucleic acid and having a double-stranded region and a proximal and a distal single-stranded homopolymer regions; a capture oligonucleotide tethered to solid support and hybridized to the proximal single-stranded homopolymer region, thereby capturing the linear molecule on the solid support; an oligonucleotide primer hybridized to the distal single-stranded homopolymer region of; and a sequencing polymerase.

BRIEF DESCRIPTION OF THE DRAWINGS

FIG. 8F shows an analysis of the components of the assembled sequencing library when the components are added as shown in FIGS. 8A-8E. Only when the beads, the capture probe, and the library molecule were all included were all three detected in the final assembled complex.

DETAILED DESCRIPTION OF THE INVENTION

Definitions

Figure 1:
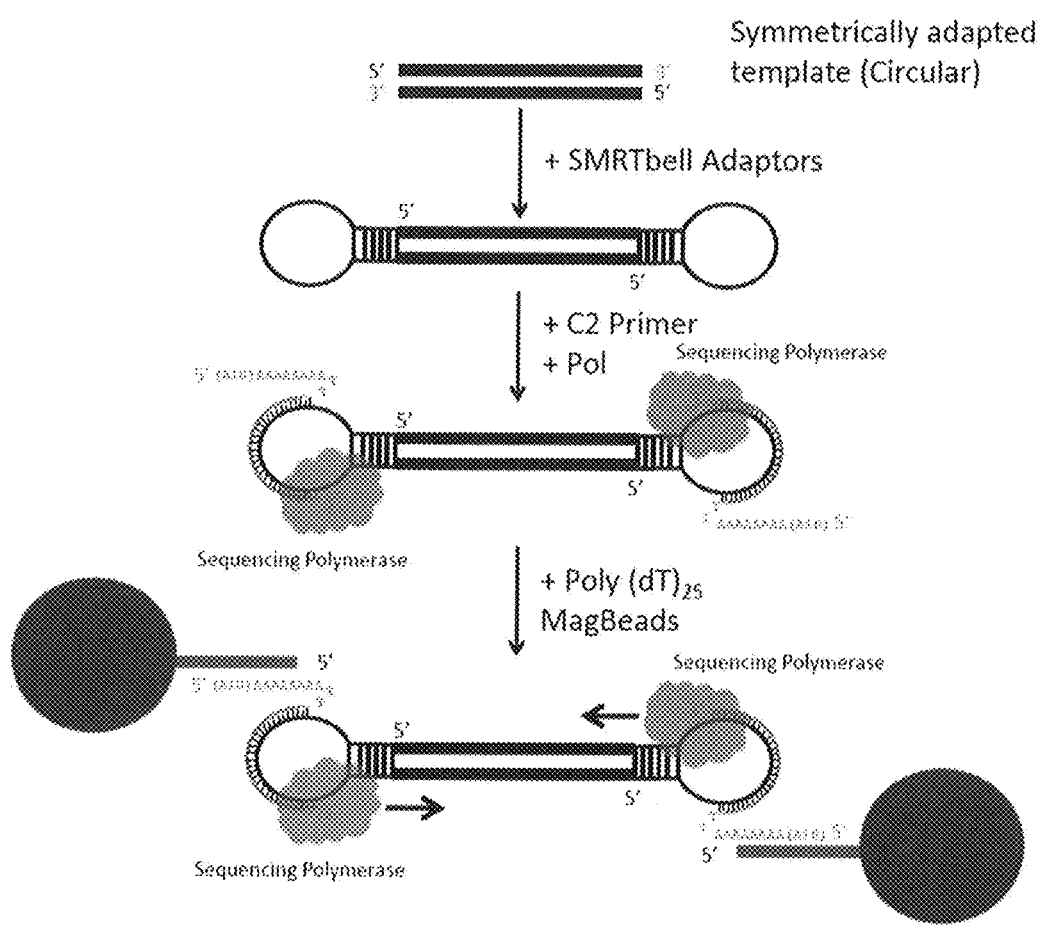
FIG. 1 shows a prior art method of making and sequencing circular templates. Capture probes hybridized to the adaptors comprise the sequence set forth as SEQ ID NO:7 plus additional sequences complimentary to the hairpin regions of the adaptors.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

A term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. An oligonucleotide may be comprised of at least 6 nucleotides or about 15-30 nucleotides. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 10 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, in vitro added to) different target nucleic acids. The universal priming site is added to the plurality of target nucleic acids using adaptors or using target-specific (non-universal) primers having the universal priming site in the 5'-portion. The universal primer can bind to and direct primer extension from the universal priming site.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "sequencing" refers to any method of determining the sequence of nucleotides in the target nucleic acid.

In some embodiments, the present invention is a method converting a double-stranded target nucleic acid into a circular locked strand template structure useful in sequencing. The use of circular templates is known in the art and has several advantages in sequencing by synthesis applications. See U.S. Pat. Nos. 7,302,146 and 8,153,375 and FIG. 1. If a strand displacing polymerase is used, it will engage in rolling circle replication, i.e., continuously displace the nascent strand and perform multiple rounds of copying the circular template. The ability to sequence (read through) the target multiple times and compare both Watson and Crick strands of the target nucleic acid linked into the circular structure allows to generate error-free or low-error consensus sequences.

However, the existing circular templates are designed to have an adaptor ligated to both ends of the target nucleic acid. (FIG. 1). Each adaptor has a binding site for the sequencing primer allowing the binding of two sequencing primers and two sequencing polymerases to each circular template. Once the sequencing reaction has started, the two polymerases have the potential to interfere with each other and cause stalling or termination of synthesis, decreasing read-length and the yield of sequencing data. This is especially problematic with shorter templates. In some applications, such as single-molecule sequencing by synthesis, the presence of two polymerases per detection point (e.g., a nanopore or a Zero Molecular Waveguide (ZMW)) will reduce the quality of the sequencing data.

Figure 2:
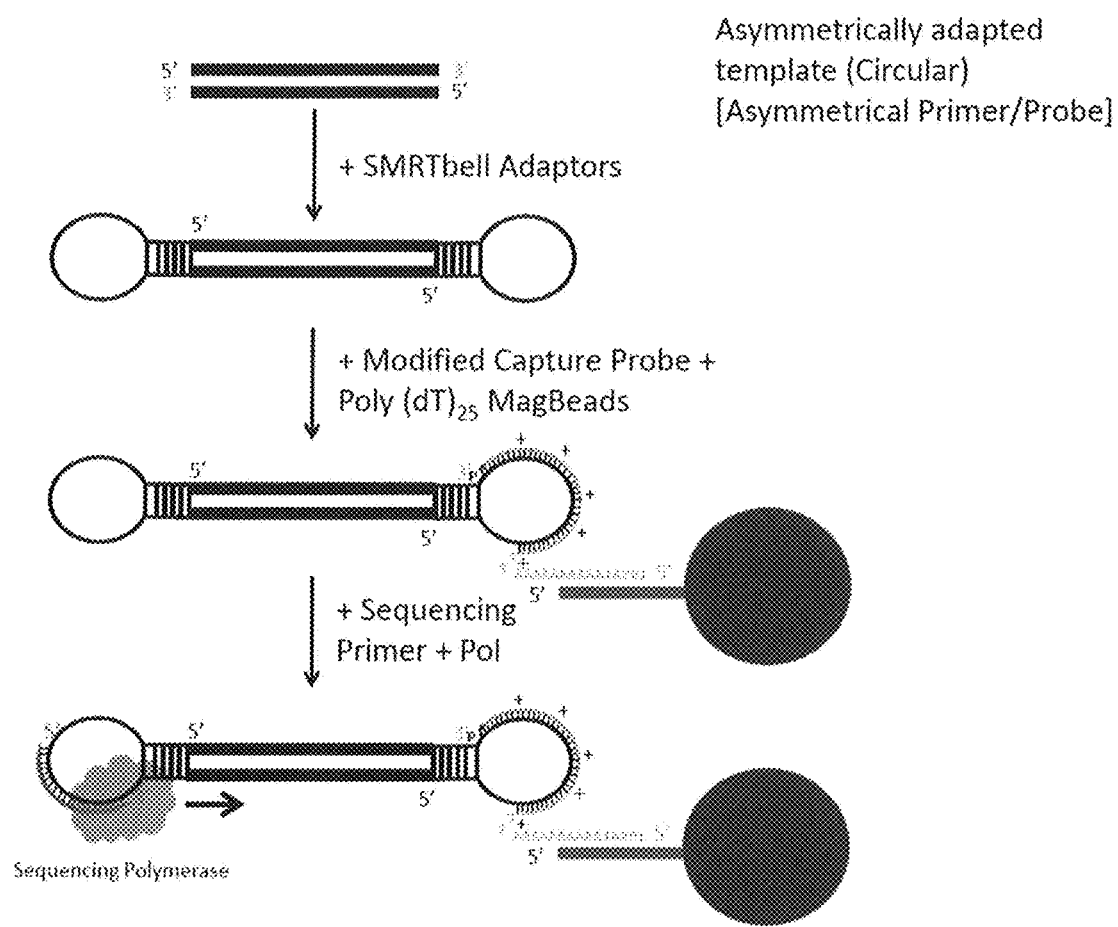
FIG. 2 shows one embodiment of the method of the invention. Capture probes hybridized to the adaptors comprise the sequence set forth as SEQ ID NO:8 plus additional sequences complimentary to the hairpin regions of the adaptors.

The present invention improves upon the existing technology by assuring that only a single sequencing polymerase is bound to each sequencing template and synthesis proceeds in only one direction. (FIG. 2). The present invention is a novel method that may increase sequencing quality, read-length and efficiency. In the embodiments of the invention, the double-stranded target nucleic acid is conjugated to two adaptors, one on each end of the molecule. Each adaptor sequence has a primer binding site (e.g., a universal primer binding site) where sequencing is to be initiated. The resulting joint molecule is captured at one end while the second end remains available for the sequencing polymerase. (FIG. 2).

The invention is a method of creating a template for sequencing a target nucleic acid or a library of target nucleic acids. In some embodiments, in the first step, the target nucleic acid is contacted with stem-loop adaptor molecules comprising a double-stranded stem region and a single-stranded loop region. Each end of the target nucleic acid is ligated to the adaptor thereby forming a joint molecule. If the adaptor has a stem-loop structure, the resulting joint molecule has a double-stranded region (comprising the target nucleic acid) and a proximal single-stranded loop region and a distal single-stranded loop region covalently linked to the double-stranded region. The joint molecule is a topologically dosed circular molecule composed of a single continuous strand. In some embodiments, the non-ligated adaptors and the non-ligated target nucleic acids are removed from the sample prior to further processing.

In some embodiments, all adaptor molecules are the same. In other embodiments, a mixture of two adaptor molecules is present. In the case of an equal mixture of two adaptors, (e.g., A and B), 50% of the joint molecules will have the desired asymmetric adaptor structure (e.g., A-B).

The joint molecule is then contacted with a limiting concentration of blocking oligonucleotides tethered to solid support. The blocking oligonucleotides may also be referred to as "capture oligonucleotides" because they may be used to capture the joint molecule, e.g., in solution or on the solid support. Capture may comprise simply forming a hybridization complex with the capture oligonucleotide or capture may comprise capturing on a solid support to which the capture oligonucleotides may be tethered. A limiting concentration of the blocking oligonucleotide is used to ensure that only one of the two adaptor-ends becomes captured or blocked while the other adaptor-end remains accessible to further enzymatic steps. In embodiments where each joint molecule has two different adaptors, the capture oligonucleotide is complementary to only one and not the other adaptor ensuring that only one of the adaptor-ends is captured. In embodiments where each joint molecule has the same adaptor on both ends, the blocking oligonucleotide is complementary to the adaptor. The use of limiting concentration of the blocking oligonucleotides ensures that only one of the adaptor-ends is captured and the other remains accessible. For convenience, in this disclosure the captured adaptor-end is designated as proximal and the free adaptor-end is designated as distal.

As will be apparent from the next steps described below, the blocking capture oligonucleotide must be non-extendable by a nucleic acid polymerase at its 3'-end. The capture oligonucleotide is at least partially complementary to the proximal adaptor-end and hybridizes to the single-stranded portion of the adaptor-end thereby blocking the adaptor-end. Because the 3'-end of the blocking oligonucleotide is non-extendable, it may not serve as a start of strand polymerization in the presence of a nucleic acid polymerase. Optionally, the non-captured joint molecules can be removed prior to the next steps.

Next, the sample is contacted with an oligonucleotide primer complementary to the primer binding site in the single-stranded region of the adaptor. Because the proximal end is blocked, only the distal end is available for primer binding and hybridization. The primer can be extended with a sequencing polymerase thereby determining the sequence of the double-stranded target nucleic acid. The sequencing is sequencing by synthesis, including single molecule sequencing or any sequencing of nucleic acids or nucleic acid derivatives. The sequencing technology may include PacBio® RS System, a nanopore sequencing system, or tunneling recognition sequencing system or any sequencing system where continuous reading of a template is possible and desired.

In some embodiments, primer extension is performed by a strand-displacing polymerase. In some embodiments, primer extension occurs via rolling circle replication enabling each template to be read multiple times by a single polymerase.

In some embodiments of the method, the adaptor flanking the ends of the target nucleic acid is a single-stranded homopolymer region. Instead of ligating adaptors to the ends of the target nucleic acid as described in the above embodiments the extendable 3'-ends of the target nucleic acid are extended by contacting the sample with a suitable enzyme and a single extendable nucleotide species. The suitable enzyme is a template-independent DNA polymerase, such as e.g., terminal deoxynucleotide transferase (TdT). Sequential addition of one species of nucleotide generates the homopolymer regions on both sides of the target nucleic acid. In some embodiments, the method includes means for controlling the size of the homopolymer region. Controlling can be accomplished by presence in the reaction of a terminator nucleotide species at a ratio favoring the extendable nucleotide, or the time of the incorporation reaction. A suitable enzyme may be a terminal transferase.

In this embodiment, the joint molecule is a linear molecule comprising the target nucleic acid and having a double-stranded region and a proximal and a distal single-stranded homopolymer region. In this embodiment, the capture oligonucleotide may be complementary to the homopolymer regions and is able to capture the single-stranded homopolymer regions thereby capturing the linear joint molecule on solid support. The homopolymer region captured on the solid support is referred to as a proximal region and the free region is a distal region. As in other embodiments of the invention, the sequencing primer is able to bind and hybridize to the free distal homopolymer region and initiate primer extension. In some embodiments, the method further comprises a step of removing the nucleic acids not captured on the solid support.

In some embodiments, each linear molecule has two different homopolymers created by sequentially blocking one end of the target nucleic acid while extending the other end with a different nucleotide. In such embodiments, the capture oligonucleotide and the primer are complementary to the homopolymers on the opposite side of the joint molecule.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples), The sample may comprise whole blood or blood fractions where tumor cells may be present. In some embodiments, the sample, especially a liquid sample may comprise cell-free material such as cell-free DNA or RNA including cell-free tumor DNA or tumor RNA. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method. Longer target nucleic acids may be fragmented although in some applications, longer target nucleic acids may be desired to achieve a longer read. In some embodiments, the target nucleic acid is naturally fragmented, e.g., circulating cell-free DNA (cfDNA) or chemically degraded DNA such as the one founds in preserved samples.

In some embodiments of the present invention, the adaptor molecules are ligated to the target nucleic acid. The ligation can be a blunt-end ligation or a more efficient cohesive-end ligation. The target nucleic acid or the adaptors may be rendered blunt-ended by strand-filling, i.e., extending a 3'-terminus by a DNA polymerase to eliminate a 5'-overhang. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In each of the above embodiments, the adaptor molecule may acquire the desired ends (blunt, single-base extension or multi-base overhang) by design of the synthetic adaptor oligonucleotides further described below. In some embodiments, other enzymatic steps may be required to accomplish the ligation. In some embodiments, a polynucleotide kinase may be used to add 5'-phosphates to the target nucleic acid molecules and adaptor molecules.

The present invention comprises the use of adaptor molecules to be ligated to one or both ends of the target nucleic acid. In some embodiments, the adaptor is a single strand of nucleic acid adopting a stem-loop secondary structure comprising at least one double-stranded and at least one single-stranded region. The double-stranded region comprises a region of at least partial self-complementarity ensuring the stability of the secondary structure under reaction conditions employed herein. In some embodiments, the adaptor molecules are in vitro synthesized artificial sequences. In other embodiments, the adaptor molecules are in vitro synthesized naturally-occurring sequences known to possess the desired secondary structure. In yet other embodiments, the adaptor molecules are isolated naturally occurring molecules or isolated non naturally-occurring molecules.

In some embodiments, the adaptor comprises at least one double-stranded region and at least one single-stranded region. In some embodiments the adaptor forms a stem-loop secondary structure with at least one double-stranded stem and at least one single-stranded loop. In some embodiments, the double-stranded stem is used for ligation to the double-stranded target nucleic acid. In other embodiments, the single-stranded portion of the adaptor is ligated to the single-stranded portion of the target nucleic acid. In some embodiments, ligating single-stranded nucleic acids is performed using splint oligonucleotides see e.g., U.S. Application Pub. No. 20120003657. In other embodiments, ligating single-stranded nucleic acids or partially single-stranded nucleic acids is performed using 5'- and 3'-end single stranded regions (overhangs) see e.g., U.S. Application Pub. No. 20140193860.

In some embodiments, the adaptor comprises one or more barcodes: a multiplex sample ID (MID), a unique ID (UID) or a combination of a UID and an MID. In some embodiments, a single barcode is used as both UID and MID.

In some embodiments, the adaptor comprises a primer binding site for a universal primer, e.g., a universal sequencing primer. In some embodiments, the adaptor comprises a binding site for a capture oligonucleotide. In some embodiments, the adaptor used in the method of the invention is a mixture of adaptors comprising a binding site for a primer and adaptors comprising a binding site for a capture oligonucleotide.

In some embodiments, the present invention comprises the use of a capture oligonucleotide. In some embodiments, the capture oligonucleotide is directly bound to a solid support. In this embodiment, the capture oligonucleotide comprises a binding moiety on one end and a free terminus on the other end. The capture oligonucleotide is tethered to solid support (e.g., bead, microsphere) via the binding moiety. In some embodiments, the tethered end of oligonucleotide comprises biotin and the solid support is coated with streptavidin. In other embodiments, the tethered end of oligonucleotide comprises a capture molecule and the solid support comprises an antibody specific for the capture molecule. For example, digoxigenin and anti-digoxigenin antibody can be used.

Figure 3:
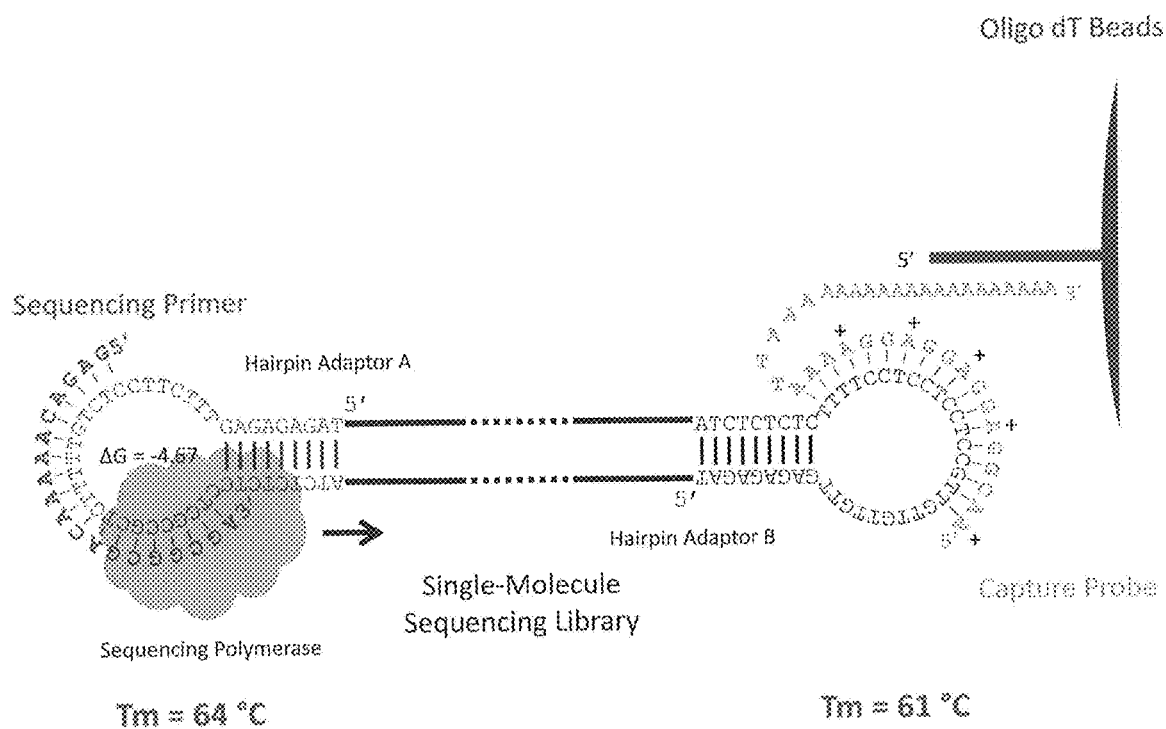
FIG. 3 shows details of the nucleotide sequence detail of the structures diagrammed in FIG. 2. Hairpin adaptor A comprises the sequence set forth in SEQ ID NO:1. Hairpin adaptor B comprises the sequence set forth in SEQ ID NO:2. The capture probe is set forth as SEQ ID NO:4. The sequencing primer is set forth as SEQ ID NO:5.
Figure 6:
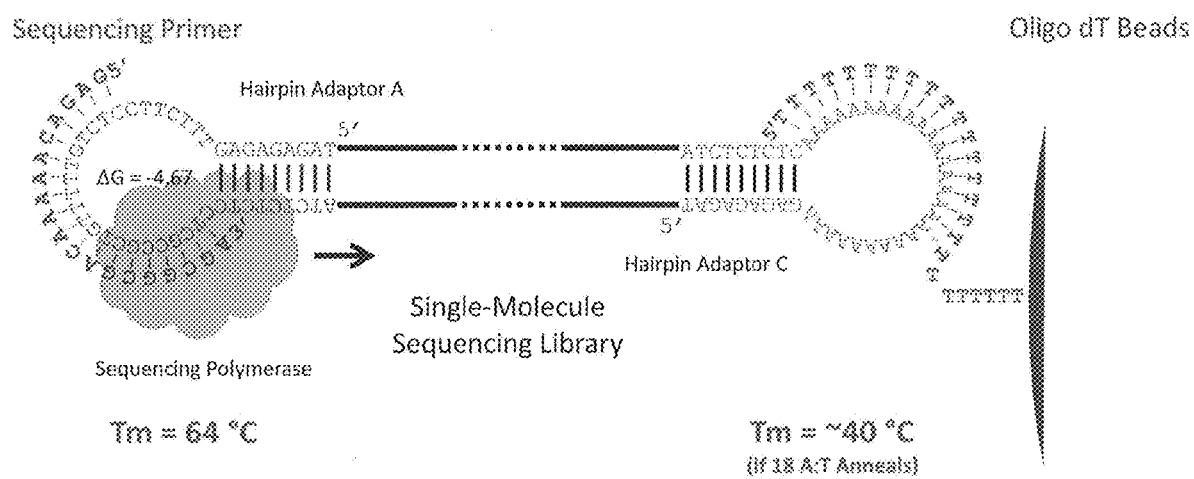
FIG. 6 shows details of the nucleotide sequence detail of another embodiment of the structures diagrammed in FIG. 2. Hairpin adaptor A comprises the sequence set forth in SEQ ID NO:1. Hairpin adaptor C comprises the sequence set forth in SEQ ID NO:3. The capture probe is set forth as SEQ ID NO:4. The sequencing primer is set forth as SEQ ID NO:5.
Figure 7:
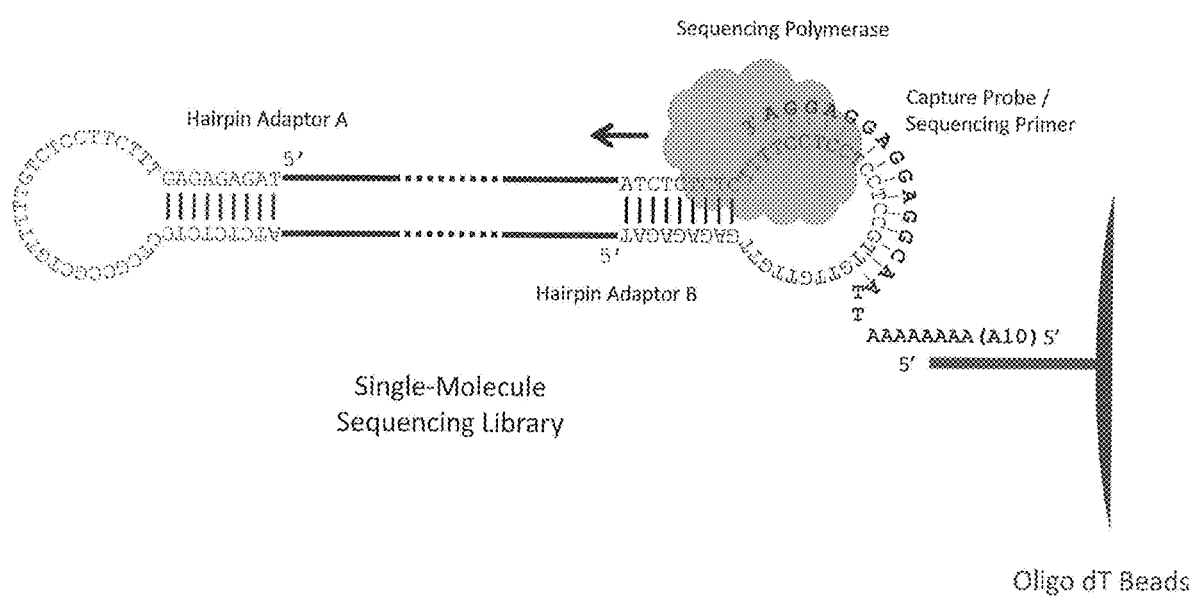
FIG. 7 shows details of the nucleotide sequence detail of another embodiment of the structures diagrammed in FIG. 2. Hairpin adaptor A comprises the sequence set forth in SEQ ID NO:1. Hairpin adaptor B comprises the sequence set forth in SEQ ID NO:2. The capture probe/sequencing primer is set forth as SEQ ID NO:6.

In some embodiment, the capture oligonucleotide is not bound to the solid support directly but is hybridized to another oligonucleotide ("bead oligonucleotide") directly linked to the solid support by any of the methods described above. The capture oligonucleotide and the bead oligonucleotide share at least one region of complementarity. For example, the bead oligonucleotide may comprise a homopolymer of dT (oligo-dT) while a portion of the capture oligonucleotide is a homopolymer of dA (oligo-dA). (FIGS. 3, 6, and 7).

In some embodiments, the blocking oligonucleotide is non-extendable by a nucleic acid polymerase at the 3'-end. The 3'-end may be rendered non-extendable by a chemical modification. For example, 3'-H, 2'-phosphate and 3'-phosphate are such modifications. The blocking oligonucleotide may have a modification preventing binding of a nucleic acid polymerase, e.g., a bulky adduct sterically blocking the 3'-end. The blocking oligonucleotide may be rendered non-extendable by virtue of being linked to the solid support via its 3'-end. The blocking oligonucleotide may also comprise one or more modifications blocking nuclease digestion such as a phosphorothioate backbone.

In some embodiments, the oligonucleotide comprises a free 5'-end and has a 3'-end tethered to the solid support. In other embodiments, the oligonucleotide comprises a free 3'-end and has a 5'-end tethered to the solid support. At least a portion of the free 5'-end or '3-end is complementary to a sequence in the adaptor. In some embodiments, the free end is complementary to the single-stranded portion of the adaptor, e.g., to the loop structure. Via this complementary portion, the capture oligonucleotide tethered to the solid support hybridizes to a joint molecule comprising a target nucleic acid ligated to at least one adaptor. The capture oligonucleotide may comprise one or more modifications stabilizing said hybrid. In some embodiments, the modifications are selected from Locked Nucleic Acids (LNA), Peptide Nucleic Acids (PNA), non-natural nucleotides such as 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like as described in e.g., U.S. Pat. No. 5,990,303.

In some embodiments, the method involves creation of a joint molecule. The join molecule comprises a double-stranded target nucleic acid ligated to one or more adaptor molecules. In some embodiments, the joint molecule is a topologically circular (closed) single strand comprising a double-stranded region (comprising the target nucleic acid) flanked on each end by a closed-loop single-stranded region (comprising the adaptor sequences).

In some embodiments, the joint molecule has identical ends, i.e., is ligated to two identical adaptors. In other embodiments, the joint molecule comprises different ends, each ligated to a different adaptor molecule. In some embodiments, the adaptor molecule is a mixture of two types of adaptors (e.g., A and B). Then the sample comprises a mixture of joint molecules with adaptors AA, AB and BB at a certain ratio. In some embodiments, an equal ratio of A and B is used. 50% of resulting joint molecules will have the desired structure A-B. 25% will be A-A, i.e., no binding site for the sequencing primer, and 25% will be B-B, two sites for the sequencing primer as was used in the prior art. In such instance, the present invention will offer an improvement over the prior art as ⅔ of the joint molecules (A-B) will be processed according to the improved method to generate improved reads.

In some embodiments, the joint molecule is a linear molecule comprising a double-stranded region comprising the target nucleic acid flanked on each end by an adaptor or the like sequence. In some embodiments, the adaptor is a linear double stranded molecule. In other embodiments, the adaptor can is a linear single-stranded molecule. In yet other embodiments, the double-stranded region comprising the target nucleic acid is flanked by one or two homopolymers.

In some embodiments, the invention utilizes enzymes. The enzymes include a DNA polymerase (including sequencing polymerase), a DNA ligase and a terminal transferase.

In some embodiments, the DNA polymerase possesses strand displacement activity and does not have a 5'-3'-exonuclease activity. In some embodiments, Phi29 polymerase and its derivatives are used, see U.S. Pat. Nos. 5,001,050, 5,576,204, 7,858,747 and 8,921,086.

In some embodiments, the invention also utilizes a DNA ligase. In some embodiments, T4 DNA ligase or *E. coli* DNA ligase is used.

In some embodiments, the invention also utilizes a template-independent DNA polymerase, e.g., a terminal transferase. In some embodiments, the invention uses a mammalian terminal transferase.

In some embodiments, the invention is a composition for determining a sequence of a double-stranded target nucleic acid comprising a circular joint molecule comprising the target nucleic acid and having a double-stranded region and a proximal single-stranded loop region and a distal single-stranded loop region covalently linked to the double-stranded region, the proximal region being hybridized to a blocking oligonucleotide that is non-extendable by a nucleic acid polymerase. The blocking oligonucleotide may be tethered to solid support. In some embodiments, the composition further comprises an oligonucleotide primer complementary to proximal and a distal single-stranded loop regions and optionally, a nucleic acid polymerase.

In some embodiments, the invention is a composition for determining a sequence of a double-stranded target nucleic acid comprising a linear joint molecule comprising the target nucleic acid and having a double-stranded region and a proximal and a distal single-stranded homopolymer regions, wherein the proximal homopolymer region is hybridized to a blocking oligonucleotide that is non-extendable by a nucleic acid polymerase. The blocking oligonucleotide may be tethered to solid support. In some embodiments, the composition further comprises an oligonucleotide primer complementary to proximal and a distal single-stranded loop regions and optionally, a nucleic acid polymerase.

EXAMPLES

Example 1 (Prophetic) Preparing Symmetrically Adapted Circular Joint Molecules for Sequencing with Asymmetric Loading of the Sequencing Polymerase In this experiment, the double stranded target DNA is obtained. The DNA is fragmented to suitable size in vitro or is naturally fragmented. An adaptor is a hairpin molecule having a double stranded portion and a loop portion. An identical adaptor is ligated to each end of the target DNA to create a joint molecule as described in Pacific Biosciences® Template Preparation and Sequencing Guide (2012) Pacific Biosciences of California, Inc. and U.S. Pat. No. 8,153,375. See FIG. 2A. The capture oligonucleotide is complementary to the single-stranded portion of the adaptor molecule (FIG. 2B). The capture oligonucleotide also comprises a poly-dA portion complementary to a poly-dT oligonucleotide bound to polystyrene-coated magnetic beads (DynaBeads®, ThermoFisher, Waltham, Mass.) (See FIG. 2A). The capture oligonucleotide has several LNA bases stabilizing the complex with the adaptor (See FIG. 2A and FIG. 2B). The other adaptor is consequently available for polymerase loading and sequencing initiation. A sequencing primer is complementary to the single-stranded portion of the adaptor and a sequencing polymerase is able to extend the primer thereby performing a sequencing reaction. The components are added in the order shown in FIG. 2.

The excess of joint molecules compared to the concentration of bead-bound capture oligonucleotides (high library: bead ratio) ensures a sufficient amount of joint molecules captured on only one end and having one end available for sequencing.

The sequencing proceeds as intended by the manufacturer of the instrument.

Example 2 (Prophetic) Preparing Asymmetrically Adapted Circular Joint Molecules for Sequencing In this experiment, the double stranded target DNA is obtained. The DNA is fragmented to suitable size in vitro or is naturally fragmented. An adaptor is a hairpin molecule having a double stranded portion and a loop portion. A mixture of equal amounts of two adaptors is added. Adaptors differ at least in the loop sequence. Adaptors are ligated to each end of the target DNA to create a joint molecule as described in Pacific Biosciences® Template Preparation and Sequencing Guide (2012) Pacific Biosciences of California, Inc. and U.S. Pat. No. 8,153,375. See FIG. 2A. The capture oligonucleotide is complementary to the single-stranded portion of the adaptor molecule (FIG. 2B). The capture oligonucleotide also comprises a poly-dA portion complementary to a poly-dT oligonucleotide bound to polystyrene-coated magnetic beads (DynaBeads®, ThermoFisher, Waltham, Mass.) (See FIG. 2A). The capture oligonucleotide has several LNA bases stabilizing the complex with the adaptor (See FIG. 2A and FIG. 2B). The other adaptor is consequently available for polymerase loading and sequencing initiation. A sequencing primer is complementary to the single-stranded portion of the adaptor and a sequencing polymerase is able to extend the primer thereby performing a sequencing reaction. The components are added in the order shown in FIG. 2. The sequencing proceeds as intended by the manufacturer of the instrument.

Figure 4:
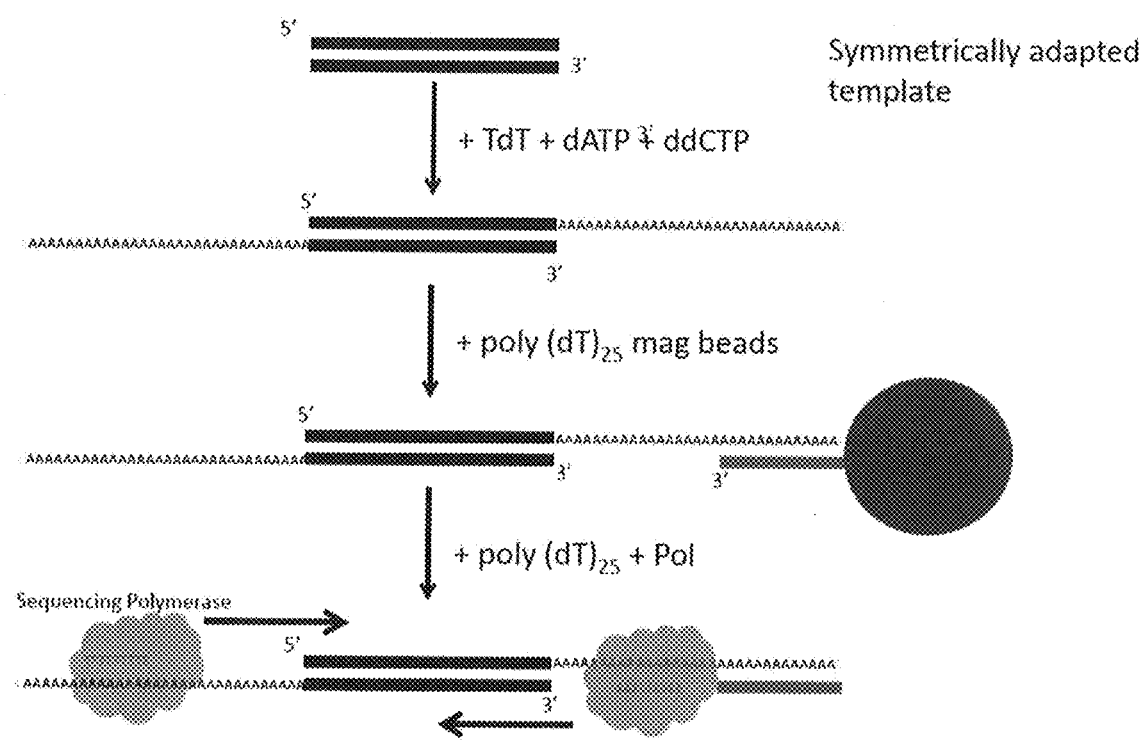
FIG. 4 shows a symmetric linear template with homopolymers (SEQ ID NO:9).
Figure 5:
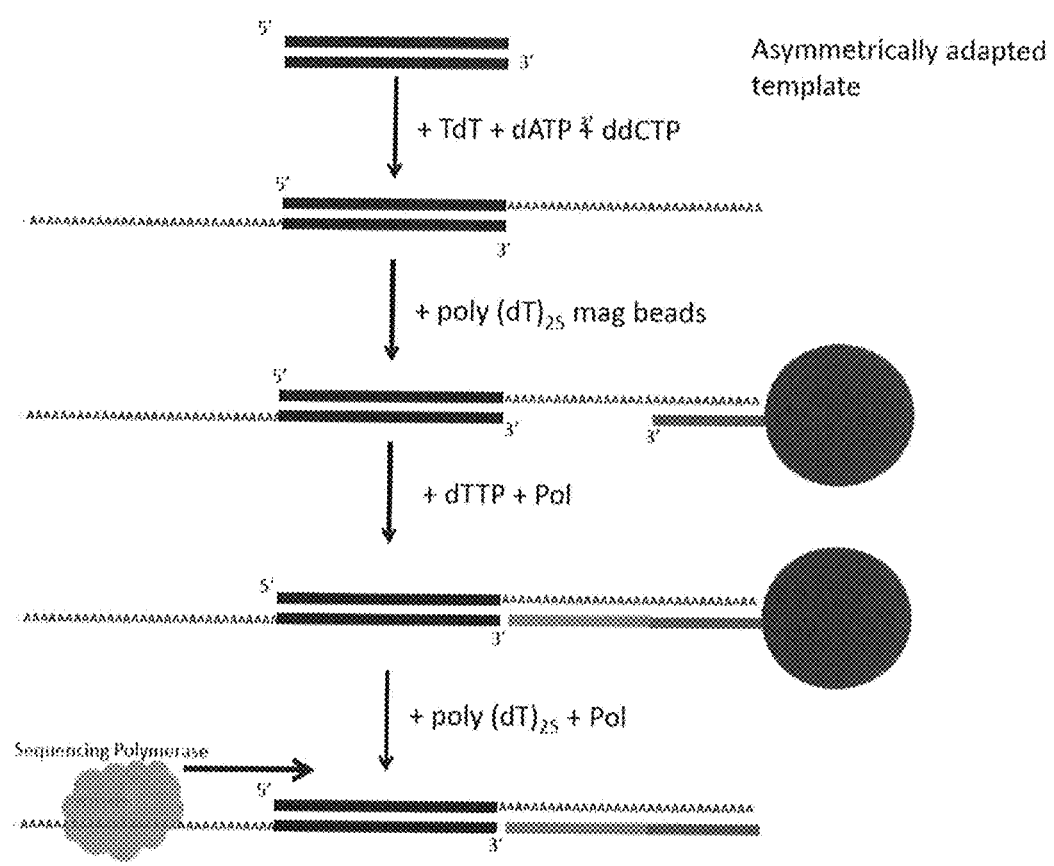
FIG. 5 shows a symmetric linear template with asymmetric loading of the sequencing polymerase. (Homopolymers set forth as SEQ ID NO:9.)

Example 3 (Prophetic) Preparing Asymmetrically Adapted Linear Joint Molecules for Sequencing In this experiment, the double stranded target DNA is obtained. The DNA is fragmented to suitable size in vitro or is naturally fragmented. Each of the 3'-ends of the target DNA is extended with terminal transferase and a single nucleotide (e.g., dATP) mixed with small amounts of a di-deoxy nucleotide (e.g., ddCTP). The target DNA has a homopolymer at each end. (FIGS. 4, 5.) The capture oligonucleotide is directly bound to a solid support and is complementary to the homopolymer (e.g., has oligo-dT) (FIGS. 4, 5). The solid support comprises polystyrene-coated magnetic beads (DynaBeads©, ThermoFisher, Waltham, Mass.) The homopolymer is available for polymerase loading and sequencing initiation.

To prevent two polymerases from loading on the same template (FIG. 4), the 3'-end of the capture oligonucleotide is extended with dTTP and a DNA polymerase to make it unavailable for the sequencing primer. The capture oligonucleotide is extended with a mixture of dTTP and ddTTP to make the extension product not further extendable. Alternatively, the capture oligonucleotide is extended with dTTP and joined with the 5'-end of the target via ligation.

Figure 8A:
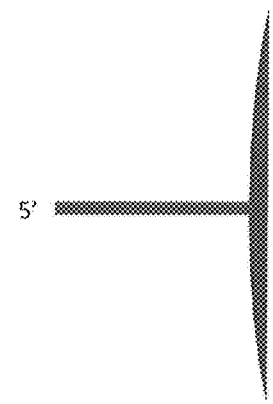
FIGS. 8A-8F show a serial assembly workflow used to prepare a sequencing library for sequencing according to the methods of the invention. The workflow starts with oligo-DT capture beads (FIG. 8A). Capture probes (SEQ ID NO:4) are added to the capture beads to form capture probe-capture bead complexes (FIG. 8B). Circular sequencing templates comprising a double-stranded target nucleic acid molecule and two hairpin adaptors (Hairpin adaptors A and B, comprising SEQ ID NOs:1 and 2, respectively) is contacted with the capture probe-capture bead complex (FIG. 8C) to form a complex of the capture bead, capture probe, and a circular sequencing template. A sequencing primer (SEQ ID NO:5) (FIG. 8D) and a sequencing polymerase (FIG. 8E) are then added.
Figure 8B:
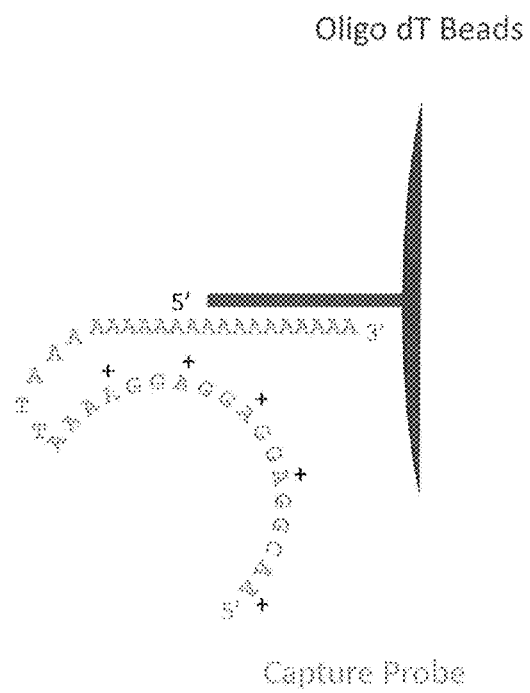
Figure 8C:
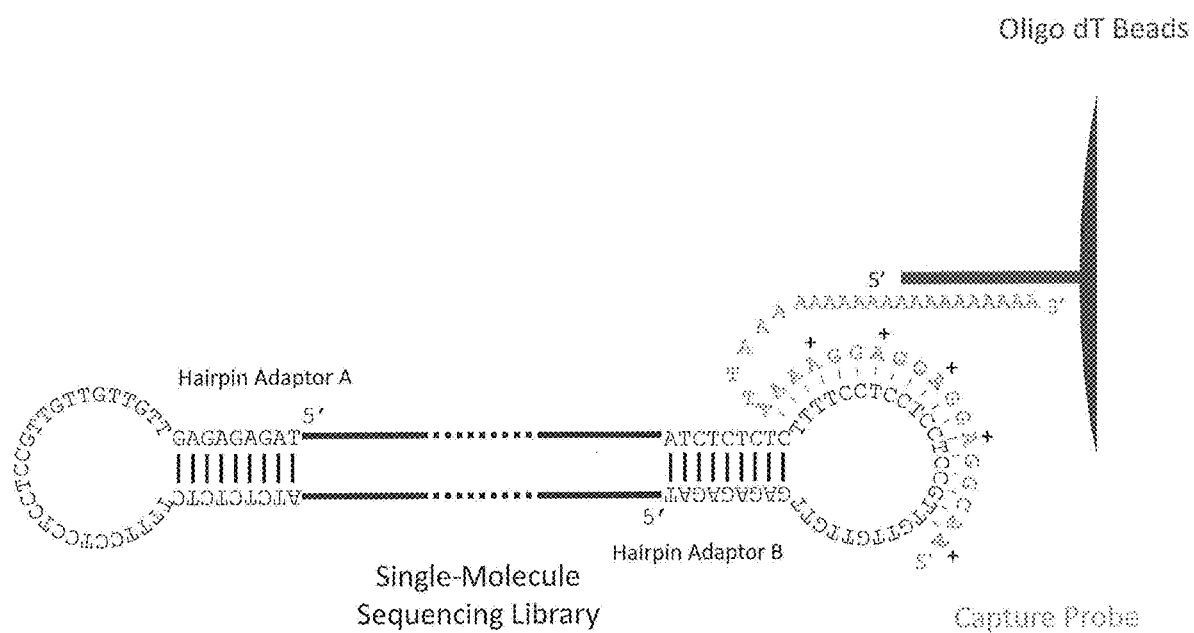
Figure 8D:
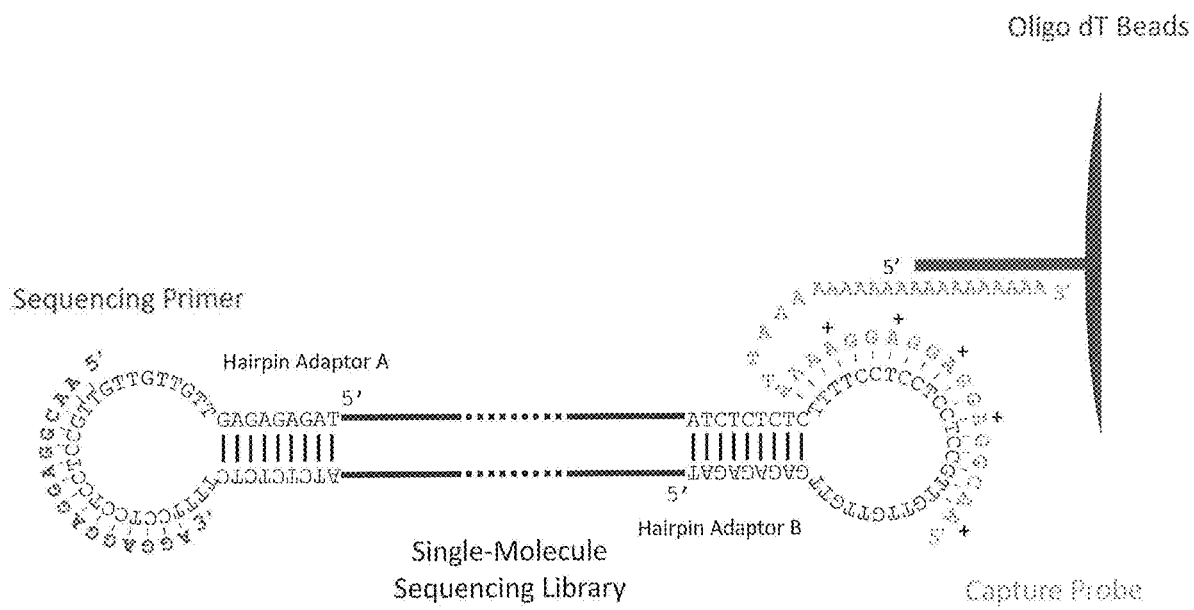
Figure 8E:
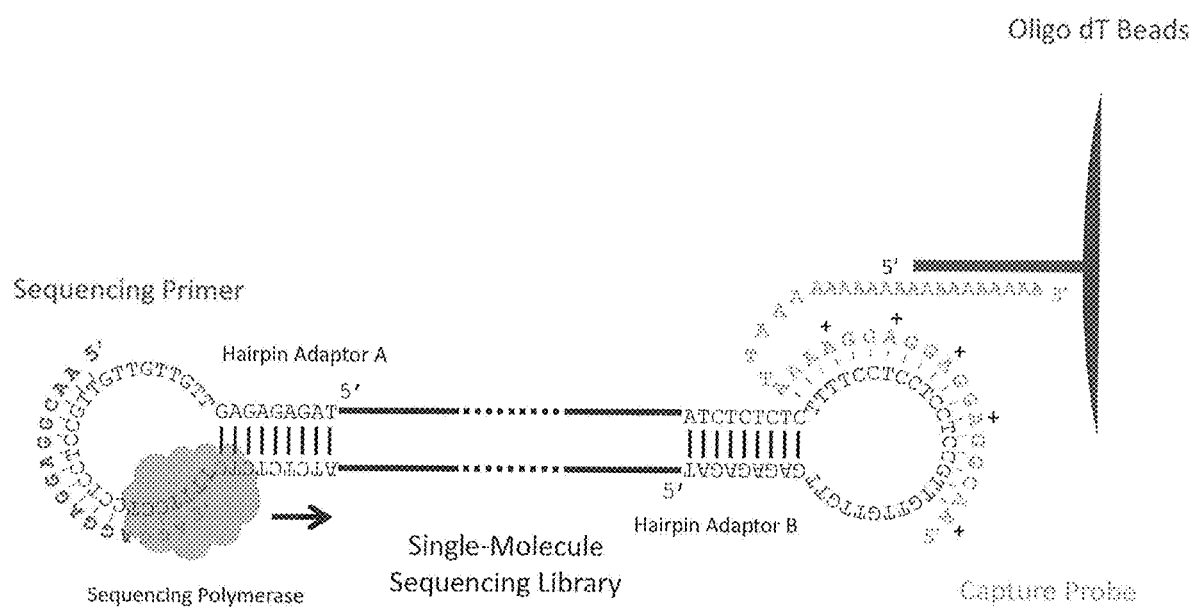
Figure 8F:
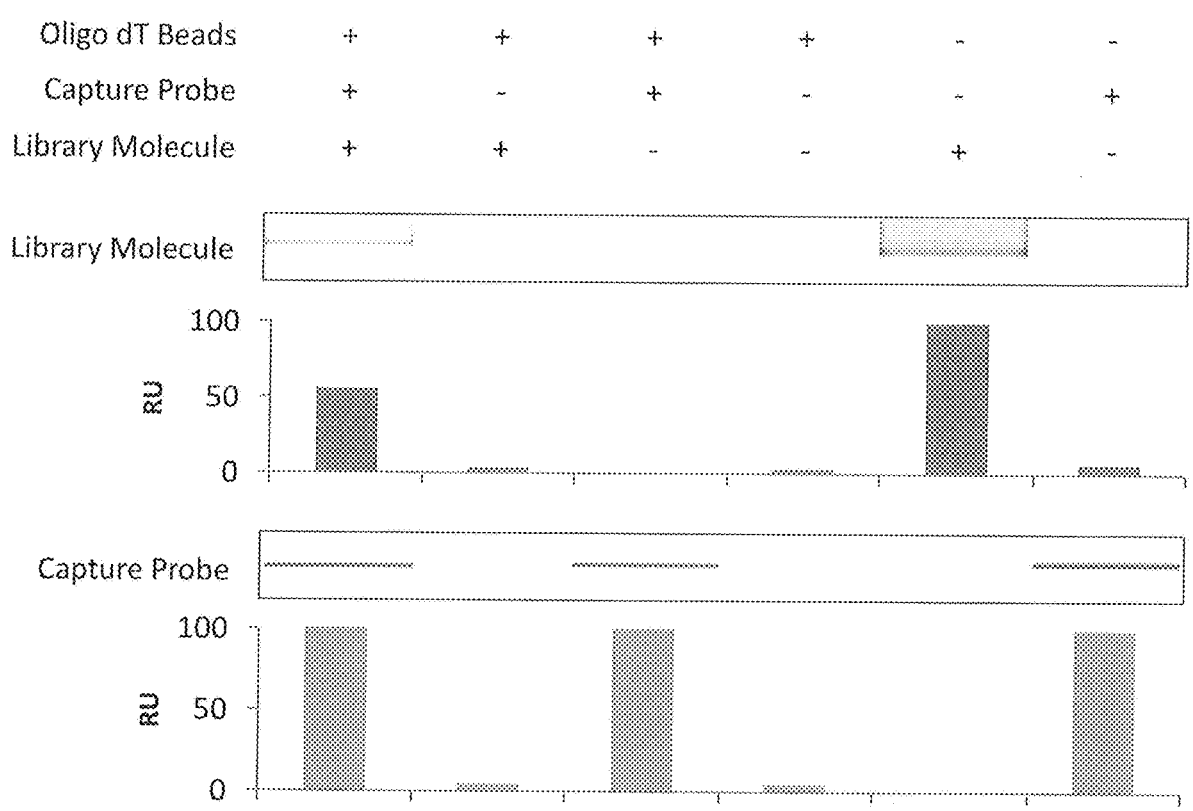

Example 4: Workflow Assembly for Asymmetrically Adapted Linear Joint Molecules for Sequencing In this experiment, shown in FIGS. 8A-8F, serial assembly workflow was used to prepare a sequencing library for sequencing according to the methods of the invention. The workflow started with oligo-DT capture beads as described above (FIG. 8A). Capture probes (SEQ ID NO:4) were added to the capture beads to form capture probe-capture bead complexes (FIG. 8B). Circular sequencing templates comprising a double-stranded target nucleic acid molecule and two hairpin adaptors (Hairpin adaptors A and B, comprising SEQ ID NOs:1 and 2, respectively) were contacted with the capture probe-capture bead complex (FIG. 8C) to form a complex of the capture bead, capture probe, and a circular sequencing template. A sequencing primer (SEQ ID NO:5) (FIG. 8D) and a sequencing polymerase (FIG. 8E)

were then added. FIG. 8F shows the results of analysis of the components of the assembled sequencing library when the components are added as shown in FIGS. 8A-8E. Only when the beads, the capture probe, and the library molecule were all included were all three detected in the final assembled complex.

Only one of the two homopolymers is now available for polymerase loading and sequencing initiation. A sequencing primer is complementary to the homopolymer (e.g., has oligo-dT) and a sequencing polymerase is able to extend the primer thereby performing a sequencing reaction. The components are added in the order shown in FIG. 2. The sequencing proceeds as intended by the manufacturer of the instrument.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of determining a sequence of double-stranded target nucleic acid in a sample, comprising:
   (a) contacting the sample comprising the double-stranded target nucleic acid with hairpin adaptor molecules comprising a double-stranded stem region and a single-stranded loop region;
   (b) ligating each terminus of the target nucleic acid molecule to the double-stranded region of the adaptor molecule, thereby forming a circular joint molecule comprising the target nucleic acid and having a double-stranded region and a proximal single-stranded loop region and a distal single-stranded loop region covalently linked to the double-stranded region;
   (c) contacting the sample with a limiting concentration of blocking oligonucleotides tethered to a solid support, wherein the blocking oligonucleotide is non-extendible by a nucleic acid polymerase and is complementary to the proximal single-stranded loop region, thereby capturing the circular joint molecule on the solid support and blocking the proximal single-stranded loop region;
   (d) contacting the sample with an oligonucleotide primer complementary to the distal single-stranded loop region, thereby hybridizing the primer to the distal single-stranded loop region; and
   (e) extending the primer with a sequencing polymerase, thereby determining the sequence of the double-stranded target nucleic acid.

2. The method of claim 1, wherein the termini of the target nucleic acid and the adaptor are rendered cohesive by enzymatic treatment.

3. The method of claim 1, wherein the blocking oligonucleotide is tethered to the solid support via means selected from a covalent bond with a support molecule or a non-covalent bond with a support molecule.

4. The method of claim 3, wherein the non-covalent bond with a support molecule is a specific interaction selected from biotin-streptavidin, antibody-antigen, or hybridization of the blocking oligonucleotide to a complementary oligonucleotide covalently or non-covalently linked to the solid support.

5. The method of claim 1, wherein the blocking oligonucleotide is rendered non-extendable by the nucleic acid polymerase by a chemical modification selected from 3'-H, 2'-phosphate, and 3'-phosphate.

6. The method of claim 1, wherein the blocking oligonucleotide has a modification preventing binding of a nucleic acid polymerase.

7. The method of claim 1, wherein the blocking oligonucleotide is non-extendable by a nucleic acid polymerase by virtue of being linked to the solid support via its 3'-end.

8. The method of claim 1, wherein the blocking oligonucleotide comprises one or more duplex stabilizing modifications.

9. The method of claim 1, wherein the blocking oligonucleotide comprises one or more modifications blocking nuclease digestion.

10. The method of claim 1, wherein the solid support is comprised of particles and each particle is linked to multiple blocker oligonucleotides.

11. The method of claim 1, further comprising, after step (c), removing the joint molecules not captured on the solid support.

12. The method of claim 1, wherein extending the primer is by a strand displacing polymerase.

13. A method of determining a sequence of a double-stranded target nucleic acid in a sample, comprising:
   (a) contacting the sample comprising the double-stranded target nucleic acid with a mixture of first and second hairpin adaptor molecules, each comprising a double-stranded stem region and a first single-stranded loop region or a second single-stranded loop region;
   (b) ligating each terminus of the target nucleic acid molecule to the double-stranded region of the adaptor molecules, thereby forming a circular joint molecule comprising the target nucleic acid and having a double-stranded region and the first single-stranded loop region on one end and the second single-stranded loop region on the other end covalently linked to the double-stranded region;
   (c) contacting the sample with a limiting concentration of blocking oligonucleotides tethered to a solid support, wherein the blocking oligonucleotide is non-extendable by a nucleic acid polymerase and is complementary to the single-stranded loop region, thereby capturing the circular molecule on the solid support and blocking the single-stranded loop region;
   (d) contacting the sample with an oligonucleotide primer complementary to the second single-stranded loop region, thereby hybridizing the primer to the second single-stranded loop region; and
   (e) extending the primer with a sequencing polymerase, thereby determining the sequence of the double-stranded target nucleic acid.

14. A composition for determining a sequence of a double-stranded target nucleic acid comprising:
   (a) a circular joint molecule comprising the target nucleic acid ligated to each end to an adaptor molecule comprising a double-stranded stem region and a single-stranded loop region, the circular joint molecule having a double-stranded region and a proximal single-stranded loop region, and a distal single-stranded loop region covalently linked to the double-stranded region;
   (b) a blocking oligonucleotide tethered to a solid support, wherein the blocking oligonucleotide is non-extendable by a nucleic acid polymerase and is hybridized to the proximal single-stranded loop region, thereby capturing the circular joint molecule on the solid support and blocking the proximal single-stranded loop region;
   (c) an oligonucleotide primer hybridized to the distal single-stranded loop region; and
   (d) a sequencing polymerase.

15. The method of claim 8, wherein the one or more duplex stabilizing modifications is selected from linked nucleic acid (LNA), peptide nucleic acid (PNA), and a non-natural nucleotide.

* * * * *

SEQUENCE LISTING

```
<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: hairpin adaptor A

<400> SEQUENCE: 1
atctctctcc tcgccgctgt ttttgtctcc ttctttgaga gagat          45

<210> SEQ ID NO 2
<211> LENGTH: 45
<212> TYPE: DNA
<213> ORGANISM: Artificial Sequence
<220> FEATURE:
<223> OTHER INFORMATION: hairpin adaptor B

<400> SEQUENCE: 2
atctctctct tttcctcctc ctccgttgtt gttgttgaga gagat          45

<210> SEQ ID NO 3
<211> LENGTH: 45
<212> TYPE: DNA
<213> ORGANISM: Artificial Sequence
<220> FEATURE:
<223> OTHER INFORMATION: hairpin adaptor C

<400> SEQUENCE: 3
atctctctca aaaaaaaaa aaaaaaaaaa aaaaagaga gagat          45

<210> SEQ ID NO 4
<211> LENGTH: 40
<212> TYPE: DNA
<213> ORGANISM: Artificial Sequence
<220> FEATURE:
<223> OTHER INFORMATION: capture probe
<220> FEATURE:
<221> NAME/KEY: misc_feature
<222> LOCATION: (1)..(1)
<223> OTHER INFORMATION: LNA-modified alanine
<220> FEATURE:
<221> NAME/KEY: misc_feature
<222> LOCATION: (6)..(6)
<223> OTHER INFORMATION: LNA-modified alanine
<220> FEATURE:
<221> NAME/KEY: misc_feature
<222> LOCATION: (9)..(9)
<223> OTHER INFORMATION: LNA-modified alanine
<220> FEATURE:
<221> NAME/KEY: misc_feature
<222> LOCATION: (12)..(12)
<223> OTHER INFORMATION: LNA-modified alanine
<220> FEATURE:
<221> NAME/KEY: misc_feature
<222> LOCATION: (15)..(15)
<223> OTHER INFORMATION: LNA-modified alanine
```

```
<400> SEQUENCE: 4
nacggnggng gnggnaaatt aaaaaaaaaa aaaaaaaaa                      40

<210> SEQ ID NO 5
<211> LENGTH: 19
<212> TYPE: DNA
<213> ORGANISM: Artificial Sequence
<220> FEATURE:
<223> OTHER INFORMATION: sequencing primer

<400> SEQUENCE: 5
gagacaaaaa cagcggcga                                            19

<210> SEQ ID NO 6
<211> LENGTH: 35
<212> TYPE: DNA
<213> ORGANISM: Artificial Sequence
<220> FEATURE:
<223> OTHER INFORMATION: capture probe / sequencing primer

<400> SEQUENCE: 6
aaaaaaaaaa aaaaaaaatt aacggaggag gagga                          35

<210> SEQ ID NO 7
<211> LENGTH: 20
<212> TYPE: DNA
<213> ORGANISM: Artificial Sequence
<220> FEATURE:
<223> OTHER INFORMATION: partial capture probe sequence

<400> SEQUENCE: 7
aaaaaaaaaa aaaaaaaatt                                           20

<210> SEQ ID NO 8
<211> LENGTH: 30
<212> TYPE: DNA
<213> ORGANISM: Artificial Sequence
<220> FEATURE:
<223> OTHER INFORMATION: partial capture probe sequence

<400> SEQUENCE: 8
aaaaaaaaaa aaaaaaaaaa aaaaaaaatt                                30

<210> SEQ ID NO 9
<211> LENGTH: 31
<212> TYPE: DNA
<213> ORGANISM: Artificial Sequence
<220> FEATURE:
<223> OTHER INFORMATION: poly-A homopolymer

<400> SEQUENCE: 9
aaaaaaaaaa aaaaaaaaaa aaaaaaaaaa a                              31

<210> SEQ ID NO 10
<211> LENGTH: 25
<212> TYPE: DNA
<213> ORGANISM: Artificial Sequence
<220> FEATURE:
<223> OTHER INFORMATION: poly-T capture sequence

<400> SEQUENCE: 10
tttttttttt tttttttttt ttttt                                     25
```